(12) United States Patent
Martikka et al.

(10) Patent No.: US 9,999,360 B2
(45) Date of Patent: Jun. 19, 2018

(54) COUPLING AND METHOD FOR DETECTING HEART RATE

(75) Inventors: Mikko Martikka, Vantaa (FI); Erik Lindman, Espoo (FI); Jari Akkila, Helsinki (FI)

(73) Assignee: SUUNTO OY, Vantaa (FI)

( * ) Notice: Subject to any disclaimer, the term of this patent is extended or adjusted under 35 U.S.C. 154(b) by 1557 days.

(21) Appl. No.: 12/482,004

(22) Filed: Jun. 10, 2009

(65) Prior Publication Data

US 2009/0312657 A1 Dec. 17, 2009

(30) Foreign Application Priority Data

Jun. 11, 2008 (FI) .................................. 20085575

(51) Int. Cl.
*A61B 5/024* (2006.01)
*A61B 5/0245* (2006.01)
*A61B 5/00* (2006.01)

(52) U.S. Cl.
CPC ........ *A61B 5/02438* (2013.01); *A61B 5/0245* (2013.01); *A61B 5/6831* (2013.01); *A61B 5/7225* (2013.01); *A61B 5/7239* (2013.01)

(58) Field of Classification Search
CPC . A61B 5/02438; A61B 5/6831; A61B 5/7239; A61B 5/0245; A61B 5/7225

USPC ....... 600/300, 508, 518, 519, 521; 607/9, 25
See application file for complete search history.

(56) References Cited

U.S. PATENT DOCUMENTS

| | | | |
|---|---|---|---|
| 2,829,637 A | 4/1958 | McCormick | |
| 3,195,535 A | 7/1965 | Westermann | |
| 3,878,833 A | 4/1975 | Arneson et al. | |
| 4,018,219 A * | 4/1977 | Hojaiban | 600/519 |
| 4,289,142 A | 9/1981 | Kearns | |
| 5,522,396 A | 6/1996 | Langer et al. | |
| 5,738,104 A * | 4/1998 | Lo et al. | 600/521 |
| 6,491,639 B1 * | 12/2002 | Turcott | 600/508 |
| 2002/0013517 A1 * | 1/2002 | West et al. | 600/300 |

FOREIGN PATENT DOCUMENTS

| | | |
|---|---|---|
| EP | 1 852 062 A1 | 11/2007 |
| GB | 2 420 628 A | 5/2006 |

* cited by examiner

*Primary Examiner* — Christopher D Koharski
*Assistant Examiner* — Pamela M Bays
(74) *Attorney, Agent, or Firm* — Birch, Stewart, Kolasch & Birch, LLP

(57) ABSTRACT

The invention relates to a coupling and method in a heart-rate measuring apparatus. The coupling in the heart-rate measuring apparatus (10) comprises means (1, 2, 3, 4, 5) for measuring heart rate and means for wireless data transmission (7). According to the invention, the heart-rate measuring device (10) comprises means (1, 2, 3, 4, 5) implemented by analog electronics for defining the maximum value of the heart-rate signal, or a parameter proportional to it.

25 Claims, 7 Drawing Sheets

COUPLING AND METHOD FOR DETECTING HEART RATE

The invention relates to a coupling according to the preamble of claim 1 for detecting heart rate.

The invention also relates to a method for detecting heart rate.

BACKGROUND

According to the prior art, U.S. Pat. No. 5,876,350 Lo et al. discloses the filtering of a pulse signal, after AD conversion. The pulse signal thus contains disturbance in the analog stage and the digital signal requires heavy processing for the required data to be recovered from the signal for further processing.

U.S. patent application 200610094969 discloses a PQRST wave and depicts the environment, to which our invention relates.

U.S. Pat. No. 5,810,722 discloses digital ways of filtering a heart-rate signal.

SUMMARY OF THE INVENTION

The invention is intended to eliminate the drawbacks of the prior art and create an entirely new type of coupling and method for detecting a pulse.

The invention is based on using analog electronics to process the heart-rate signal to remove interference from it before it is forwarded or taken to the processor.

Thus, according to one preferred embodiment of the invention, the maximum value of the heart-rate signal is sought, using analog electronic means, from the electrical signal induced by the heart.

According to a second preferred embodiment, the detection of the maximum is confirmed with the aid of an analogically defined time derivative of the descending edge of the signal.

Further, according to a third preferred embodiment, the time stamp of the maximum is obtained from the descending edge after the maximum, for example, by sending an interrupt to a microcontroller.

According to a fourth preferred embodiment of the invention, the detected maximum is accepted as the moment of the heartbeat, if a new maximum is not detected after the detection of the maximum, during a period of a predefined number of milliseconds x (x being approx. 200-250).

According to a fifth preferred embodiment of the invention, after acceptance of the maximum, the new maximum should be at least 'previous maximum-y' mV (y being approx. 0.5).

According to a sixth preferred embodiment of the invention, if a new maximum is not detected during the maximum heart-rate interval (e.g., 2 seconds), the reference level is reset to its minimum value.

More specifically, the coupling according to the invention is characterized by what is stated in the characterizing portion of claim 1.

The method according to the invention is characterized, for its part, by what is stated in the characterizing portion of claim 11.

Considerable advantages are achieved with the aid of the invention.

With the aid of the invention, A/D conversion can be entirely avoided in the heart-rate transmitter. As a signal with less interference is obtained from the analog part of the heart-rate transmitter, in some embodiments of the invention the signal processing of the digital side of the heart-rate belt can be significantly simplified. Typically, a wristop computer will not require any separate modifications in order to implement the invention.

Known heart-rate measuring electronics using a fixed triggering voltage may cause a situation, in which the voltage caused by a contraction of the heart muscle of a person in the measurement range is small, the person will not be able to measure his heart rate using the belt in question. On the other hand, the solution according to the invention adapts substantially to the measured signal.

In the following, the invention is described with the aid of the embodiments according to the accompanying drawings.

DETAILED DESCRIPTION

Figure 1:
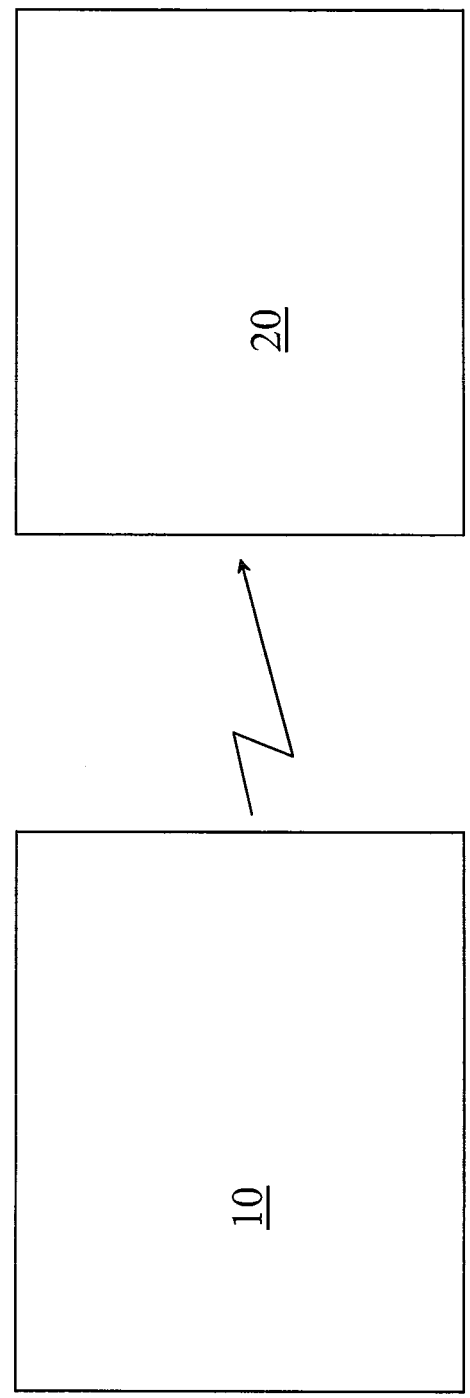
FIG. 1 shows a schematic block diagram of the environment according to the invention.

According to FIG. 1, the invention relates to an environment, in which by means of the heart-rate measuring apparatus such as a heart-rate belt 10 or similar, heart-rate data is transmitted wirelessly to a receiver device 20, for example, a wristop computer. The heart-rate measuring device 10 thus contains means for measuring heart rate, such as measuring electrodes and their related electronics, and means for forwarding the heart-rate data wirelessly. The receiver apparatus 20, for its part, comprises means for receiving heart-rate data over a wireless transmission channel, as well as means for analysing the received heart-rate data and/or displaying it and/or for displaying the result data. The receiver apparatus 20 can also act solely as a remote display for the heart-rate belt.

The central ideas of the invention is to refine the heart-rate signal in an analog form in the heart-rate transmitter 10, to be clean enough for it to be connected directly to the microcontroller of the heart-rate belt 10, or even to be transmitted in an analog form to the receiver unit 20. Thus, digital further processing in the receiver unit 20 can be made as simple as possible and, on the other hand, the heart-rate belt 10 containing the transmitter can also be made simple, economical, and reliable.

Figure 2:
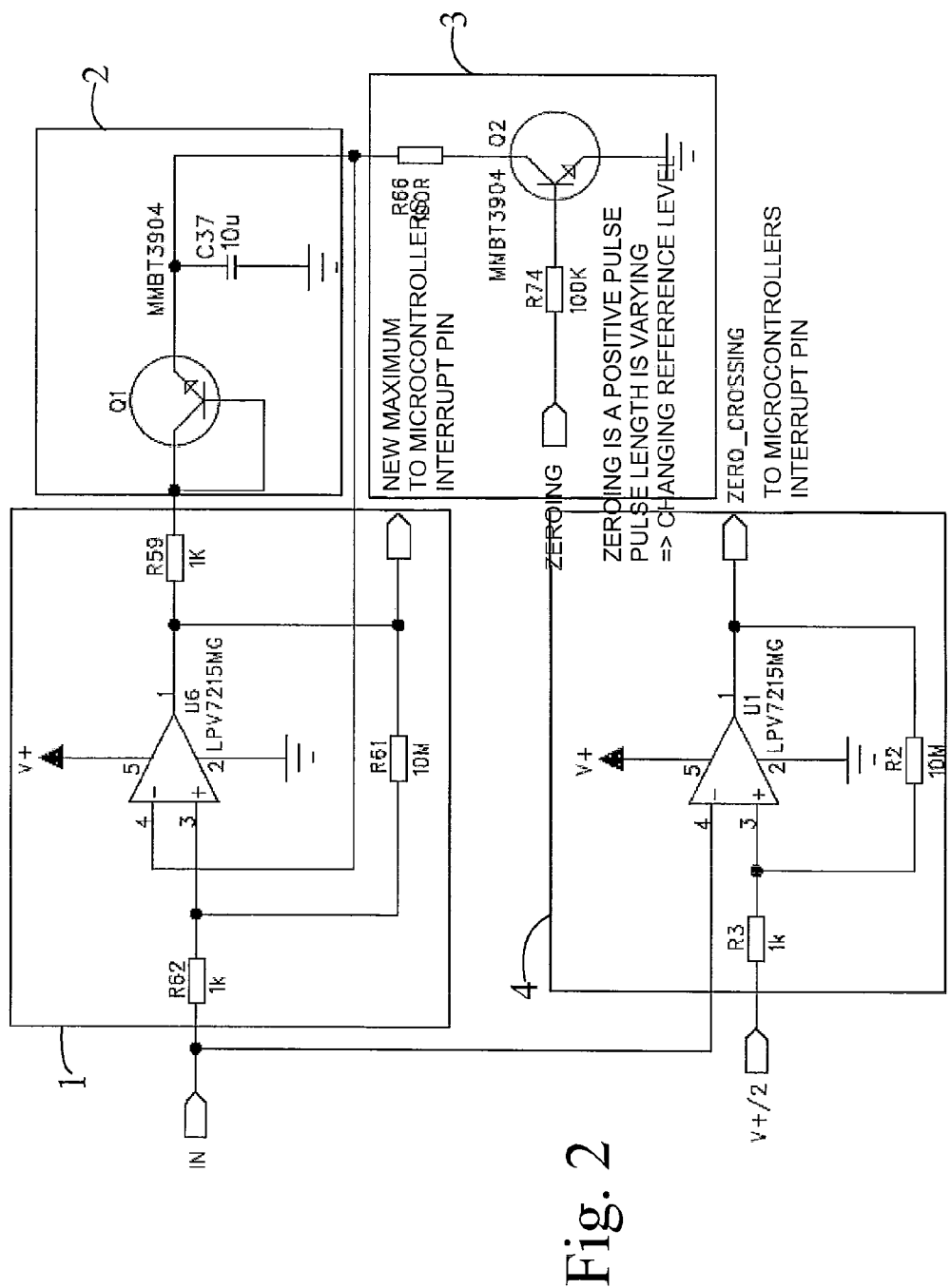
FIG. 2 shows a circuit diagram of a preferred embodiment of the invention.
Figure 3A:
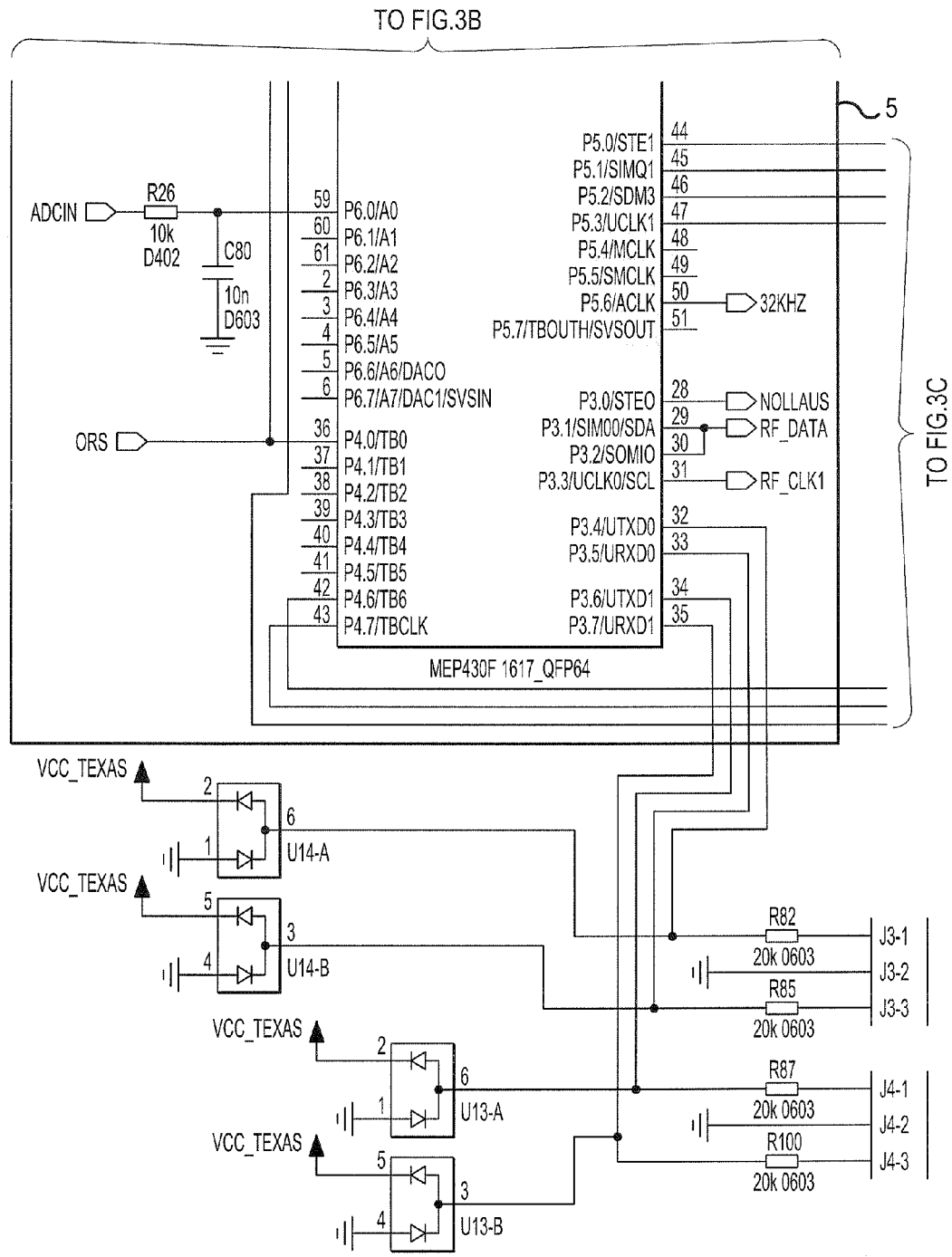
FIG. 3 shows a circuit diagram of another preferred embodiment of the invention.
Figure 3B:
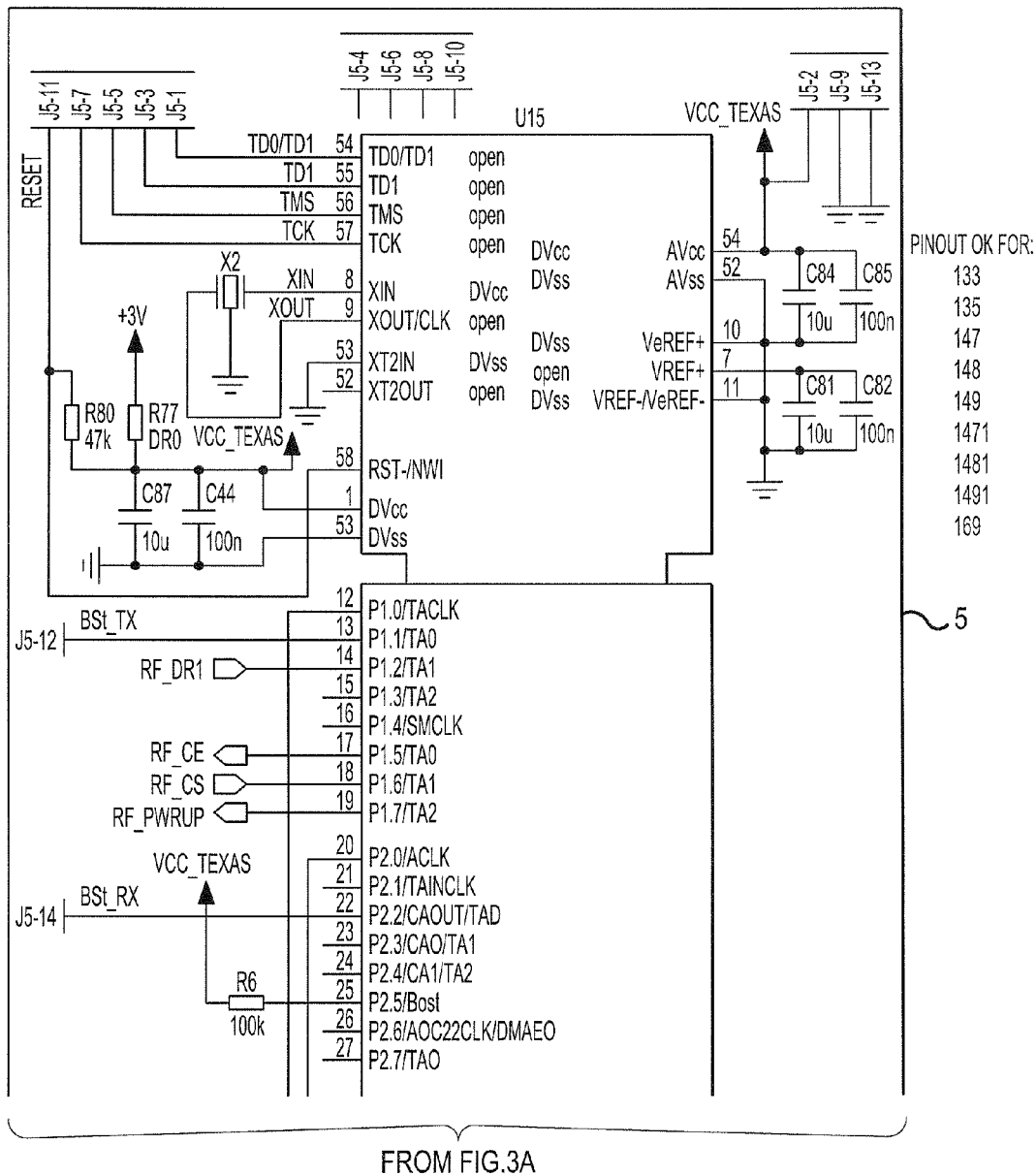
Figure 3C:
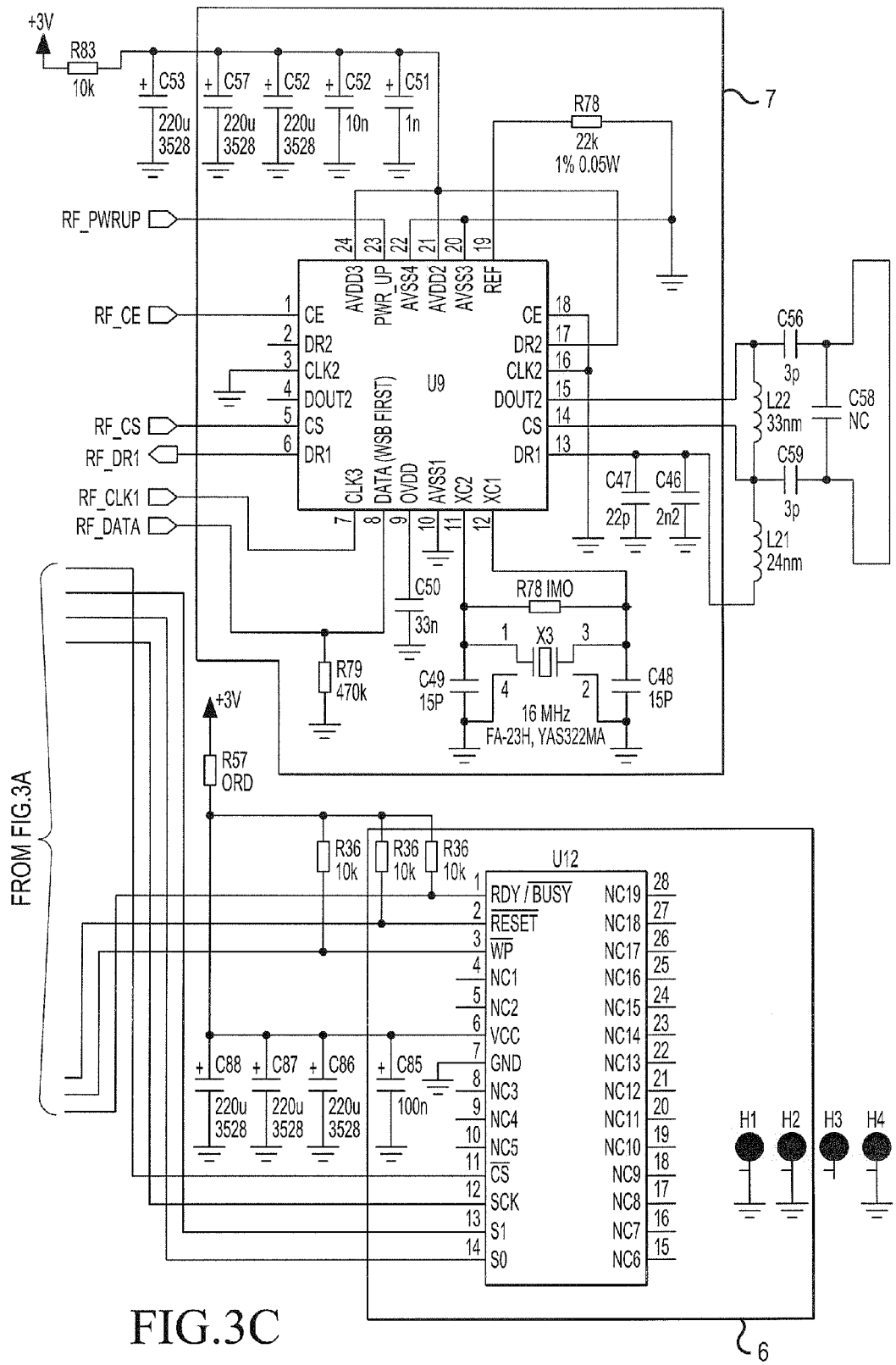

The circuits shown in FIGS. 2 and 3 are thus located in block 10 of FIG. 1.

According to FIG. 2, the detection of the maximum is implemented in block 1. Block 1 uses a comparator U6 to compare the input signal arriving at its first input 3 with the recorded previous maximum, which is obtained from the output of block 2 and is fed to the second input 4 of the comparator U6. When the input signal is greater than the previous maximum, the pulse is brought to the controller from the output 1 of the comparator U6.

In block 2, the recording of the maximum is implemented with the aid of a transistor Q1 and a capacitor C37. This block stores the maximum value of the input signal produced by the previous block 1. As stated above, the stored maximum value acts as a reference for the comparator U6 of block 1 and connects this to the second input.

Block 1 and block 2 combined form a peak detector.

In block 3, the calculation of the maximum is implemented with the aid of a transistor Q2. The longer a zero pulse is connected to the base of transistor Q2, the more the recorded maximum value will drop off. This allows the reference voltage of block 1 to be regulated by altering the length of the zero pulse. The recorded maximum value is calculated at regular intervals. The microcontroller (not shown) can alter the interval as required. When the reference voltage of block 3 is left above the zero level, in an environment with interference no new pulse will come immediately to the microcontroller.

If new maximum values do not appear within a set time, the maximum value stored in block 2 can be reset using a long zero pulse.

Block 4 acts as a zero detector. The voltage set by the microcontroller acts as a reference for the comparator U1. Here, the voltage in question is marked as half of the operating voltage, but this need not necessarily be the case. The pulse for the controller from block 4 is obtained from the RS edge descending from the QRS complex.

The pulse succeeding the maximum value of the input signal (the pulse from block 1 to the microcontroller) from block 4 (less than the reference level set by the microcontroller) represents the QRS complex.

The time stamp is recorded by the microcontroller from the pulse of both block 1 and block 4. The pulse caused by the QRS complex from block 4 comes in the known time window after the pulse coming from block 1. If it does not, it is a question of a disturbance.

Block 5 of FIG. 3 is a microcontroller. The microcontroller sets the default value for the reference voltage of block 4. If pulses occur from blocks 1 and 4 in the set time window, the time stamp of the heartbeat is recorded. The maximum voltage recorded in block 2 after the time window is calculated by block 3.

The length of the pulse going to block 3 and the reference voltage of block 4 are changed as required. After this, a new time window starts.

Block 6 is a memory. If the application records information, non-volatile memory (EPROM or flash) is used. Block 7 is a data link, by means of which the application forwards the heart-rate data wirelessly, for example, to a wristop computer.

Figure 4:
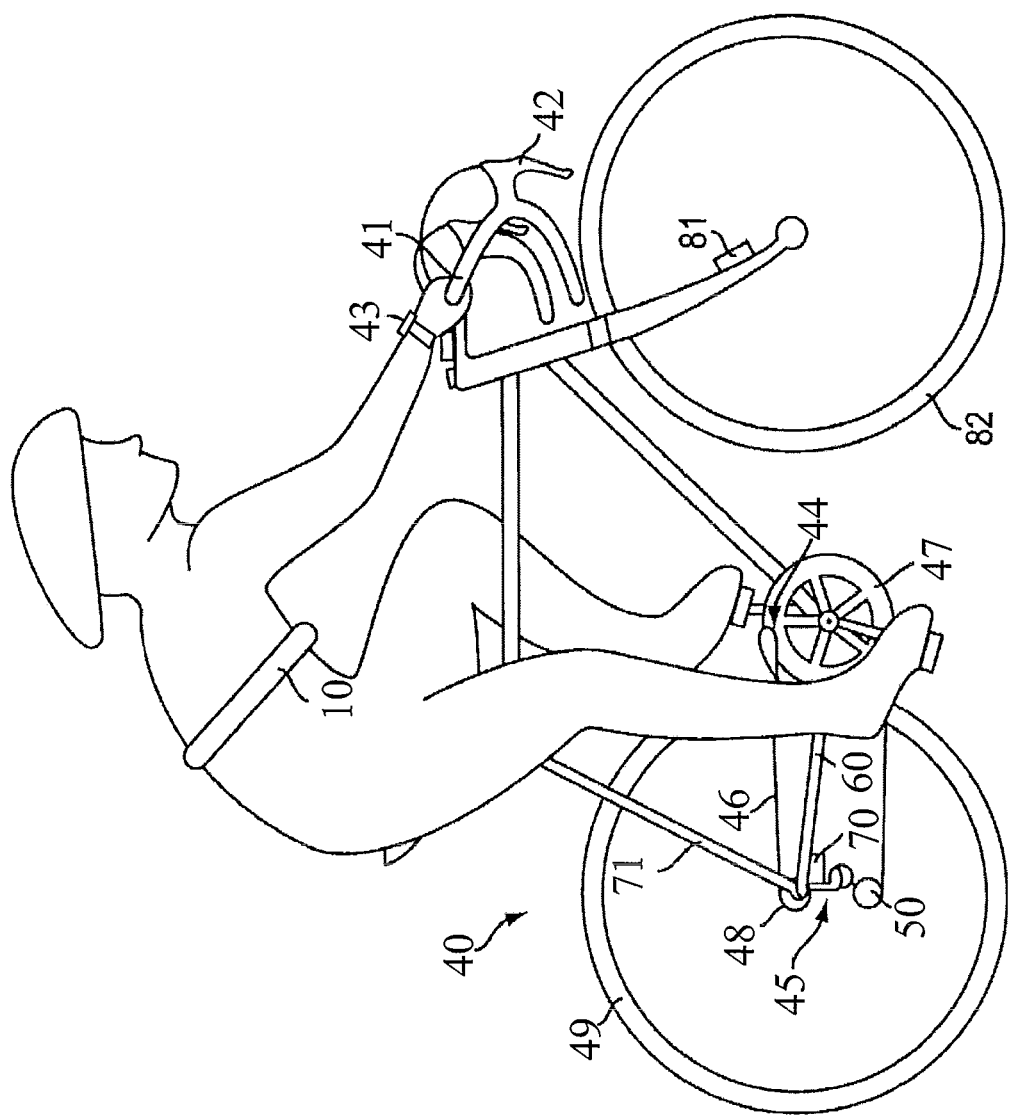
FIG. 4 shows schematically one application of the invention.

According to FIG. 4, the invention can be applied in connection with cycling, among other things, in which the bicycle 40 comprises handlebars 41 and brake levers 42 attached to them. In addition, the bicycle has normally a front gear changer 44 and a rear gear changer 45. The front gear changer 44 guides the chain to the desired front chainwheel 47 and correspondingly the rear gear changer 45 and 20 is used to guide the chain 46 to the desired rear sprocket. A measuring device 70 can be fitted in connection with the rear wheel 49 supported by the rear forks 71 and 60, for measuring the tension of the chain, or alternatively the device 70 can be used for wireless gear-changing. Correspondingly, a speedometer sensor 81, which receives its signal from a magnetic piece attached to a spoke in the front wheel 82, can be fitted in connection with the front wheel 82.

Thus, according to the invention, the devices in connection with the wristop computer 43 acting as the receiver device, in this case the heart-rate belt 10, the device 70, and/or the speedometer sensor 81 are used to form, with the aid of the analog electronics, a definition of the signal's maximum value, or a parameter proportional to it, before the signal is transmitted to be digitized, or before its transmission to the wristop computer 43. In a cycling application, the wristop computer 43 corresponding to the receiver 20 of FIG. 1 can be able to be attached to the handlebars 41, or alternatively the receiver can be a pure cycling computer attachable to the handlebars with a quick-release lock.

Figure 5:
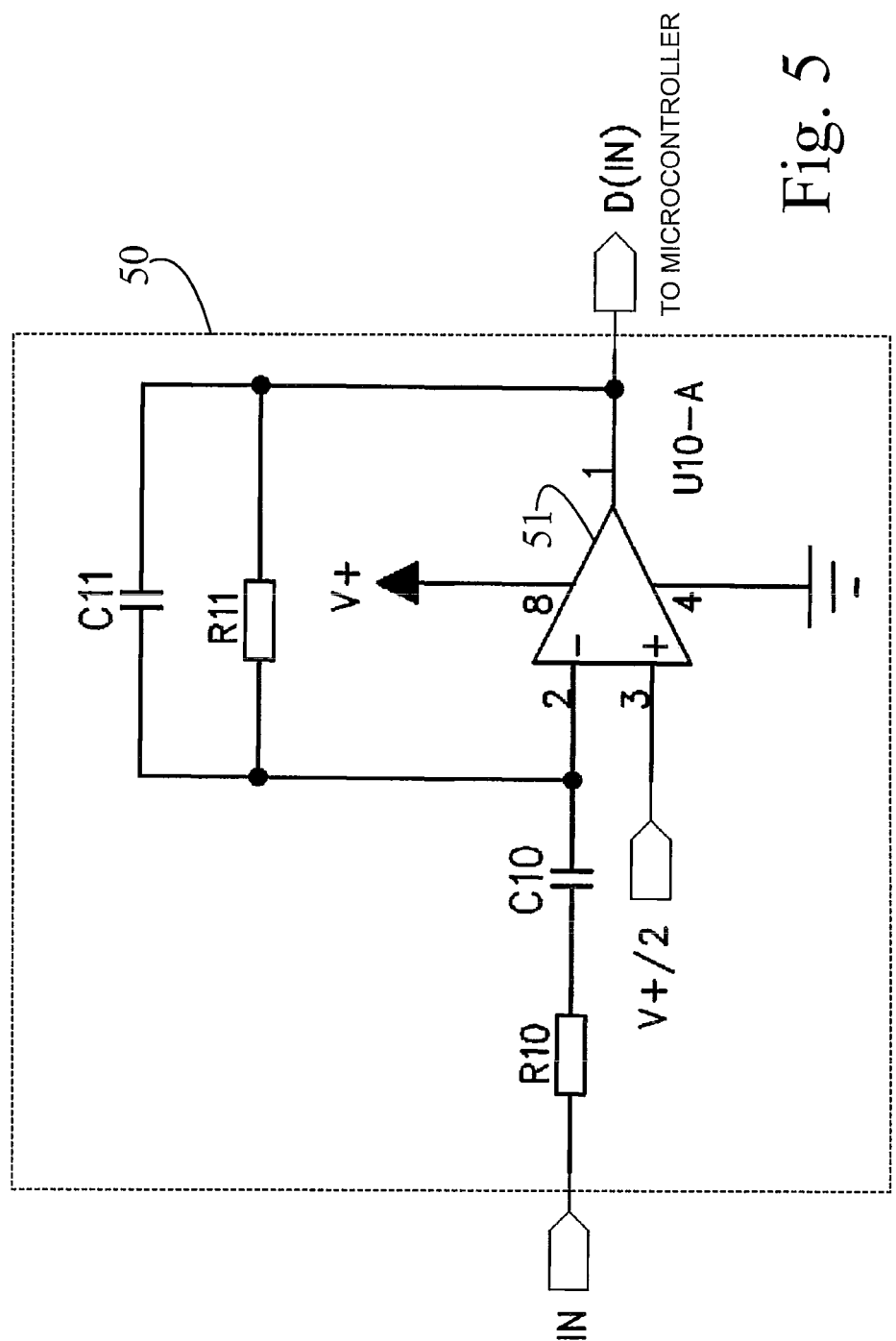
FIG. 5 shows a circuit diagram of one application according to the invention.

According to FIG. 5, the means implemented by analog technology for confirming the detection of a maximum with the aid of a time derivative of the descending edge of the signal can be implemented, for example, by a differentiator 50, which is connected between the input IN and the microcontroller of FIG. 2 (e.g., FIG. 3, block 5). In practice, the differentiator is formed of an operational amplifier 51, the output and negative input of which are connected as feedback, by a resistor R11 and a capacitor C11 connected in parallel. The positive terminal of the operational amplifier 51 is connected to a constant voltage, in this case to half of the operating voltage. Between the negative input and input IM of the operational amplifier 51, a resistor R10 and a capacitor C10 are further connected in series.

According to the invention, once a heartbeat has been detected or triggered, it can be forwarded wirelessly, for example, equipped with identifier information. Alternatively, a set of heartbeat-related time stamps, which have been produced with the aid of the invention, can be transmitted.

The form of transmission can also be such that the hear-rate/minute value is calculated and forwarded. The manner of transmission of the calculated value requires at least some detected heartbeats to be recorded in the heart-rate belt, in order to form a transmission signal. The heart-rate data need not always be transmitted to the display device or the receiver device during the performance, but can be collected in a heart-rate belt, wristop device, or cycle computer for later use.

The invention can also be applied in a heart-rate belt equipped with memory, the contents of which memory can be also downloaded wirelessly to a PC, or by wired transmission for later hear-rate-based analyses.

Various analyses, for example, of energy consumption, can be calculated in real time or afterwards from any of the devices described.

The invention claimed is:

1. Coupling in a heart-rate measuring apparatus, comprising:
   one or more electrodes for receiving a heart rate signal;
   analog circuitry configured to store a reference level proportional to a maximum value of the heart rate signal received from the electrodes;
   a peak detector configured to compare the heart rate signal received from the electrodes with the stored reference level from the analog circuitry; and
   a transmitter for wirelessly transmitting heart rate data based on output from the peak detector.

2. Coupling according to claim 1, wherein the analog circuitry that stores the reference level is connected directly to a microcontroller of the heart-rate measuring apparatus.

3. Coupling according to claim 1, further comprising analog circuitry configured to confirm the detection of a peak, using a time derivative of a descending edge of the heart rate signal.

4. Coupling according to claim 3, wherein the analog circuitry configured to confirm the detection of a peak acquires a time stamp of a peak by sending an interrupt to a microcontroller.

5. Coupling according to claim 1, further comprising circuitry for accepting a peak detected by the peak detector as a heartbeat moment, if a new peak is not detected after a predefined period.

6. Coupling according to claim 1, further comprising circuitry for accepting a maximum on a condition, wherein a new maximum is at least a previous maximum-y mV, where y is approximately 0.5.

7. Coupling according to claim 1, further comprising circuitry for resetting the reference level to a minimum value, if a peak is not detected by the peak detector during a predefined interval.

8. Coupling according to claim 1, wherein the transmitter is configured to transmit heart-rate data equipped with identifier information.

9. Coupling according to claim 1, wherein the transmitter is configured to transmit time stamps based on the output of the peak detector.

10. Coupling according to claim 1, further comprising a memory.

11. Coupling according to claim 1, further comprising a zero detector configured to detect a zero crossing in the heart rate signal received from the electrodes.

12. Coupling according to claim 1, further comprising a microcontroller configured to process heart rate data.

13. The coupling according to claim 1, wherein the analog circuitry configured to store a reference level proportional to a maximum value of the heart rate signal comprises a transistor and a capacitor.

14. Method in a heart-rate measuring apparatus, comprising:
   receiving a heart rate signal;
   storing, using analog circuitry, a reference level proportional to a maximum value of the received heart rate signal; and
   detecting a maximum in the received heart rate signal when the received signal is greater than the reference level.

15. Method according to claim 14, further comprising confirming, using analog circuitry, the detection of a maximum with the aid of a time derivative of a descending edge of the heart rate signal.

16. Method according to claim 14, further comprising acquiring a time stamp of the maximum by sending an interrupt to a microcontroller.

17. Method according to claim 14, wherein the detected maximum is accepted as the moment of a heartbeat, if, after the detection of the maximum, a new maximum is not detected during a predefined period.

18. Method according to claim 14, wherein the maximum is accepted on a condition, by which a new maximum is at least a previous maximum -y mV, where y is approximately 0.5.

19. Method according to claim 14, wherein the reference level is reset to its minimum value, if a new maximum is not detected during a predefined interval.

20. Method according to claim 14, wherein the heart rate data transmitted from the heart-rate measuring device is equipped with identifier information.

21. Method according to claim 14, wherein heart rate data is transmitted from the heart-rate measuring apparatus as time stamps relating to the heartbeats.

22. Method according to claim 14, wherein information is recorded in the heart-rate measuring apparatus.

23. Method of claim 14, further comprising detecting a zero crossing of the received heart rate signal based on a reference.

24. Heart-rate measuring system, comprising:
   a heart-rate measuring device, which includes one or more electrodes for receiving a heart rate signal, analog circuitry configured to store a reference level proportional to a maximum value of the heart rate signal received from the electrodes, and circuitry for wirelessly transmitting heart rate data, and
   a receiver apparatus, which comprises circuitry for receiving heart-rate data over a wireless transmission channel and analysing or displaying the received heart-rate data, or for displaying analysis results.

25. The heart-rate measuring system according to claim 24, wherein the analog circuitry configured to store a reference level proportional to a maximum value of the heart rate signal comprises a transistor and a capacitor.

* * * * *